(12) United States Patent
Suvkhanov et al.

(10) Patent No.: US 7,414,721 B1
(45) Date of Patent: Aug. 19, 2008

(54) IN-SITU METROLOGY SYSTEM AND METHOD FOR MONITORING METALIZATION AND OTHER THIN FILM FORMATION

(75) Inventors: Agajan Suvkhanov, Portland, OR (US); Ynhi Thi Le, Gresham, OR (US)

(73) Assignee: LSI Corporation, Milpitas, CA (US)

( * ) Notice: Subject to any disclaimer, the term of this patent is extended or adjusted under 35 U.S.C. 154(b) by 0 days.

(21) Appl. No.: 10/328,066

(22) Filed: Dec. 23, 2002

(51) Int. Cl.
*G01J 4/00* (2006.01)
(52) U.S. Cl. .................. 356/369; 356/630; 438/16
(58) Field of Classification Search ............. 438/14, 438/15, 16; 356/369, 364, 367, 368, 381, 356/382, 625–632, 484–489, 630
See application file for complete search history.

(56) References Cited

U.S. PATENT DOCUMENTS

| | | | | |
|---|---|---|---|---|
| 5,361,967 A | * | 11/1994 | Anderson et al. | 228/124.6 |
| 5,877,859 A | * | 3/1999 | Aspnes et al. | 356/364 |
| 6,080,531 A | * | 6/2000 | Carter et al. | 430/329 |
| 6,168,961 B1 | * | 1/2001 | Vaccari | 438/16 |
| 6,181,421 B1 | * | 1/2001 | Aspnes et al. | 356/369 |
| 6,268,917 B1 | * | 7/2001 | Johs | 356/369 |
| 6,275,291 B1 | * | 8/2001 | Abraham et al. | 356/367 |
| 6,320,657 B1 | * | 11/2001 | Aspnes et al. | 356/369 |
| 6,342,450 B1 | * | 1/2002 | Lattard | 438/696 |
| 6,383,724 B1 | * | 5/2002 | Carter et al. | 430/329 |
| 6,408,048 B2 | * | 6/2002 | Opsal et al. | 378/89 |
| 6,449,043 B2 | * | 9/2002 | Aspnes et al. | 356/369 |
| 6,462,817 B1 | * | 10/2002 | Strocchia-Rivera | 356/369 |
| 6,465,265 B2 | * | 10/2002 | Opsal et al. | 438/16 |
| 6,673,637 B2 | * | 1/2004 | Wack et al. | 438/14 |
| 6,694,284 B1 | * | 2/2004 | Nikoonahad et al. | 702/155 |
| 7,235,495 B2 | * | 6/2007 | Wagener | 438/756 |
| 2002/0045282 A1 | * | 4/2002 | Opsal et al. | 438/16 |
| 2005/0048800 A1 | * | 3/2005 | Wagener | 438/785 |
| 2007/0218668 A1 | * | 9/2007 | Wagener | 438/591 |

* cited by examiner

*Primary Examiner*—Laura M Schillinger
(74) *Attorney, Agent, or Firm*—Maginot, Moore & Beck

(57) ABSTRACT

An in-line, in-process or in-situ and non-destructive metrology system, apparatus and method provides composition, quality and/or thickness measurement of a thin film or multilayer thin film formed on a substrate in a thin film processing system. Particularly, the subject invention provides a spectroscopic ellipsometer performing spectroscopic ellipsometry while the wafer is in a thin film processing system. In one form, the spectroscopic ellipsometer is associated with a wet bench system portion of the thin film processing system. The spectroscopic ellipsometer obtains characteristic data regarding the formed thin film to calculate penetration depth ($D_p$) for a thin film formed on the substrate. Particularly, the ellipsometer obtains an extinction coefficient (k) which is used to calculate penetration depth ($D_p$). Penetration depth ($D_p$), being a unique function of the extinction coefficient (k) provides the information for the composition, quality and/or thickness monitoring of the thin film.

8 Claims, 4 Drawing Sheets

IN-SITU METROLOGY SYSTEM AND METHOD FOR MONITORING METALIZATION AND OTHER THIN FILM FORMATION

BACKGROUND

1. Field of the Invention

The subject invention relates generally to metrology of integrated circuit structures and, more specifically, to in-situ metrology of metalized and other thin film formation integrated circuit structures.

2. Background Information

Integrated circuits have become key components of many consumer and commercial electronic products, often replacing discrete components and enhancing product functionality. The semiconductor processing technologies that produce these integrated circuits have advanced to the point where complete systems can now be reduced to a single integrated circuit or application specific integrated circuit (ASIC) device. These integrated circuits or "chips" may incorporate many functions that previously could not be implemented together on a single chip, including but not limited to: microprocessors, digital signal processors, mixed signal and analog functions, large blocks of memory and high speed interfaces. The requisite level of integration, however, significantly complicates the design and manufacturing processes.

In the manufacture or fabrication of integrated circuits, various thin films are formed on a substrate or wafer. An example of thin film formation is metalization. One such metalization process is silicidation. Silicidation is an anneal (sintering) process of a metal thin film resulting in the formation of a metal-Si alloy. Because the correct formation of such thin films is essential to proper structure and/or functioning of the final integrated circuit (i.e. the various components of the final integrated circuit), it is prudent to examine at least some of the metalized substrates. Such examination or analysis is typically accomplished using various metrology techniques. These metrology techniques, however, are destructive to the structure (e.g. integrated circuit) under test and require a separate and additional tool. The additional to further requires more space in the lab. Moreover, these metrology techniques are performed after thin film processing (i.e. after the wafer is removed from the thin film processing system).

Particularly, various optical metrology devices have been developed for measuring and characterizing thin films on semiconductor wafers. One such tool is described in PCT application WO/9902970, published Jan. 21, 1999. This device includes a number of measurement technologies. More specifically, the device includes a beam profile ellipsometer (BPE) (see U.S. Pat. No. 5,181,080); a beam profile reflectometer (BPR) (see U.S. Pat. No. 4,999,014); relatively conventional broad band (BB) and deep ultraviolet (DUV) spectrometers; a broad band spectroscopic ellipsometer (SE) (see U.S. Pat. No. 5,877,859) and an off-axis narrow band ellipsometer (see U.S. Pat. No. 5,798,837). These various optical metrology devices, however, are stand-alone devices that are used on processed substrates remote from the processing device.

What is therefore needed in view of the above, is a system, method and/or apparatus that provides metrology of a thin film or thin film layers in the thin film processing system (in-situ).

SUMMARY

The subject invention is a system, apparatus and/or method of in-situ or in-line metrology of a thin film or thin film layers formed or being formed on a substrate or wafer for an integrated circuit. The subject invention provides non-destructive, metrological analysis of a formed or being formed thin film or thin film layers on an integrated circuit wafer while the wafer is in a thin film processing system (in-situ).

In one form, the subject invention provides a metrology system such as a spectroscopic ellipsometer in a wafer or substrate thin film processing system. The metrology system (e.g. spectroscopic ellipsometer) provides composition, thickness and/or quality measurement of a thin film or multiple layers formed on the wafer.

The spectroscopic ellipsometer is operative to obtain penetration depth for a thin film formed on a substrate or for multiple thin films formed on a substrate while the substrate is in the thin film processing system. The penetration depth provides a unique function of an extinction coefficient k. For a given extinction coefficient k and an index of refraction n, penetration depth is calculated. Penetration depth provides characteristics of the formed thin film such as at least one of thin film composition, quality, and thickness.

In one form, there is provided a method of in-situ monitoring of a thin film on a wafer for an integrated circuit. The method includes: (a) providing a metrology device in a thin film processing system that is operative to produce a thin film on a substrate; (b) producing a thin film on the substrate; (c) performing metrology on the formed thin film by the metrology device to obtain metrology data regarding the formed thin film; and (d) calculating penetration depth utilizing the obtained metrology data whereby characteristics of the formed thin film on the substrate are obtained.

In another form, the subject invention provides a method of in-situ monitoring of thin film processing of a wafer for an integrated circuit. The method includes: (a) providing a spectroscopic ellipsometer in a thin film processing system; (b) performing thin film processing on a wafer in the thin film processing system; (c) performing spectroscopic ellipsometry on the thin film processed substrate by the spectroscopic ellipsometer to obtain spectroscopic ellipsometry data regarding the thin film processed wafer; and (d) calculating penetration depth utilizing the obtained spectroscopic ellipsometry data whereby characteristics of the thin film processed wafer are obtained.

In yet another form, there is provided a thin film processing system for a wafer including a processing area operative to perform thin film processing on a wafer, and a metrology device disposed in the processing area and operative to perform metrological measurement of a thin film formed on the wafer wherein at least one of composition, quality and thickness of the formed thin film is obtained. Preferably, the metrology device is a spectroscopic ellipsometer that is operative to perform metrological measurement including obtaining an extinction coefficient (k) for calculating depth penetration ($D_p$) of the thin film according to $D_p=(\lambda/2k\pi)$.

BRIEF DESCRIPTION OF THE DRAWINGS

The above-mentioned and other features and advantages of this invention, and the manner of attaining them, will become more apparent and the invention will be better understood by reference to the following description of an embodiment of the invention taken in conjunction with the accompanying drawings, wherein.

Corresponding reference characters indicate corresponding parts throughout the several views unless specified otherwise.

DESCRIPTION OF THE PREFERRED EMBODIMENT(S)

Figure 1:
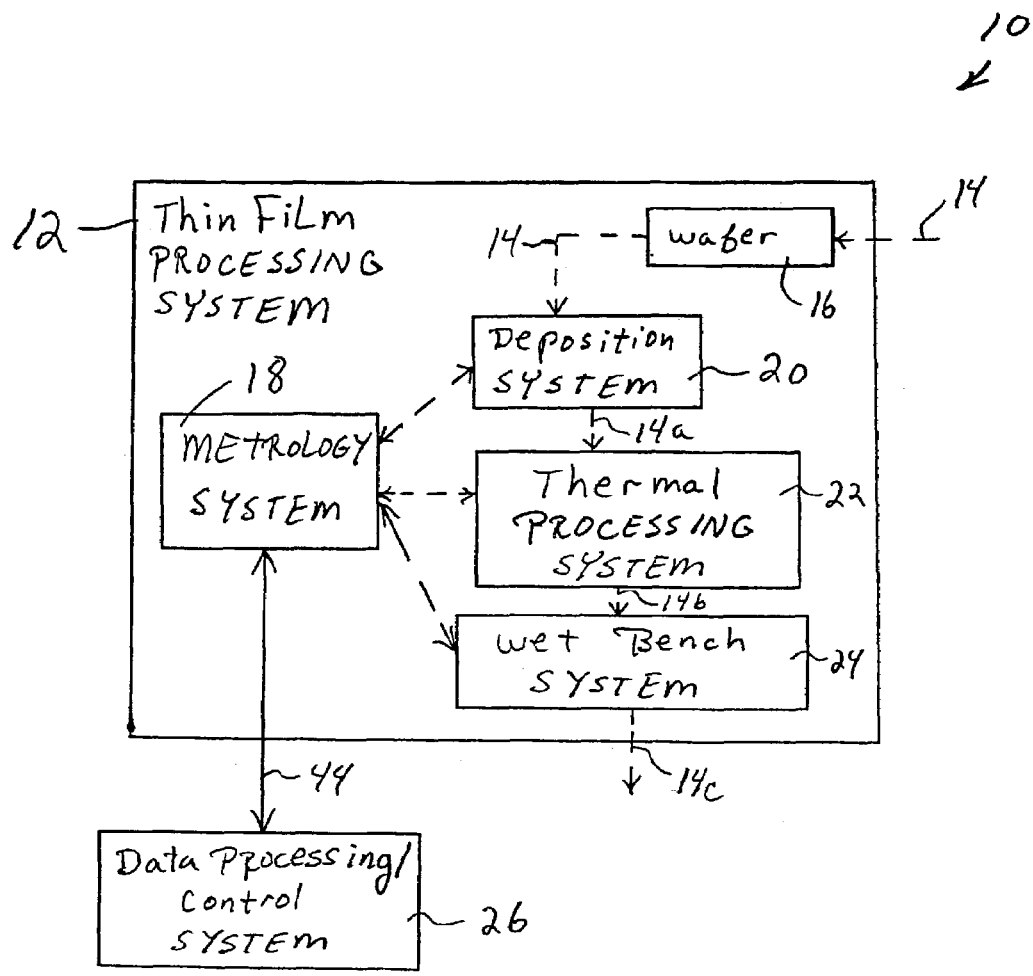
FIG. 1 is a block diagram of an exemplary thin film processing system for a wafer in accordance with the principles of the subject invention.

With reference now to FIG. 1, there is shown a wafer or substrate thin film processing system generally designated 10 incorporating an embodiment of the subject invention in accordance with the present principles. The thin film processing system 10 is representative of various types of thin film processing systems for a substrate, wafer, or the like (hereinafter collectively, "wafer"). The wafer eventually becomes one or more integrated circuits (ICs), integrated circuit chips ("chips") or the like. The thin film processing system 10 is operative to form a thin film or thin film layers on a wafer in a variety of manners such as is known in the art. The thin film processing system 10 is further operative to provide one or more types of thin films/thin film layers as is/are known in the art such as silicides.

The thin film processing system 10 includes a processing area 12 such as is known in the art for thin film processing of a wafer. The processing area 12 includes a deposition system 20, a thermal processing system 22 and a wet bench system 24. In accordance with an aspect of the subject invention, the thin film processing system 10 and/or thin film processing area 12 includes a metrology system 18. As represented by the dashed, double-headed arrows, the metrology system 18 is operative, configured and/or adapted to provide metrological measurement of a thin film and/or thin film layers of a wafer within any one or more of the systems 20, 22 and 24.

In general a wafer 16 is introduced into the processing area 12 and follows a travel path 14 to the various systems thereof. Initially, the wafer 16 is provided, via travel path 14, to the deposition system 20. The deposition system 20 is operative, configured and/or adapted to perform deposition on the wafer 16, such as is known in the art, in order to provide a thin film thereon.

According to an aspect of the subject invention, the metrology system 18 may be provided in the thin film processing area 12 and/or within the deposition system 20 such that metrological measurements may be obtained regarding the thin film while within the deposition system 20 (as represented by the dashed, double-headed arrow between the metrological system 18 and the deposition system 20). This may be done either during or after the deposition process. Metrological measurements are accomplished as detailed below.

After the wafer 16 has been processed as necessary by the deposition system 20, the wafer 16 travels via path 14a to the thermal processing system 22. The thermal processing system 22 is operative, configured and/or adapted to provide thermal processing to the wafer 16 such as is known in the art.

According to an aspect of the subject invention, the metrology system 18 may be provided in the thin film processing area 12 and/or within the thermal processing system 22 such that metrological measurements may be obtained regarding the thin film while within the thermal processing system 22 (as represented by the dashed, double-headed arrow between the metrological system 18 and the thermal processing system 22). This may be done either during or after the thermal process. Metrological measurements are accomplished as detailed below.

After the wafer 16 has been processed as necessary by the thermal processing system 22, the wafer 16 travels via path 14b to the wet bench system 24. The wet bench system 24 is operative, configured and/or adapted to provide chemical treatment/processing to the wafer 16 such as is known in the art.

According to an aspect of the subject invention, the metrology system 18 may be provided in the thin film processing area 12 and/or within the wet bench system 24 such that metrological measurements may be obtained regarding the thin film while within the wet bench system 24 (as represented by the dashed, double-headed arrow between the metrological system 18 and the thermal processing system 22). This may be done either during or after the chemical treatment process. Metrological measurements are accomplished as detailed below.

As indicated above, the thin film processing system 10/thin film area 12 also includes a metrology system 18. The metrology system 18 is operative, configured and/or adapted to provide measurement of the thin film or thin films formed on the wafer 16. The metrology system 18 is in bi-directional communication with a data processing/control system 26 via communication line 44. The data processing/control system 26 is operative, configured and/or adapted to provide control signals to the metrology system 18. The control signals allow the metrology system 18 to perform metrological analysis as described herein. The data processing/control system 26 may also provide control signals to the processing system 10/processing area 12 and its components (i.e. the deposition system 20, the thermal processing system 22, and/or the wet bench system 24) and/or to other components (not specifically shown herein) of the system 10. The metrology system 18 is operative, configured and/or adapted to obtain metrological measurements (data) with respect to the wafer 16 (substrate) and, more particularly with respect to any thin film or thin films on the wafer 16. The metrology system 18 is further operative, configured and/or adapted to provide the obtained metrological data to the data processing/control system 26. The data processing/control system 26 processes the metrological data received from the metrology system 18 in order to determine the composition and/or thickness of the formed thin film or thin films on the wafer 16. Particularly, the data processing/control system 26 processes the data received from the metrology system 18 to determine a penetration depth for the sample under test (i.e. a wafer with a thin film or thin films thereon).

Figure 2:
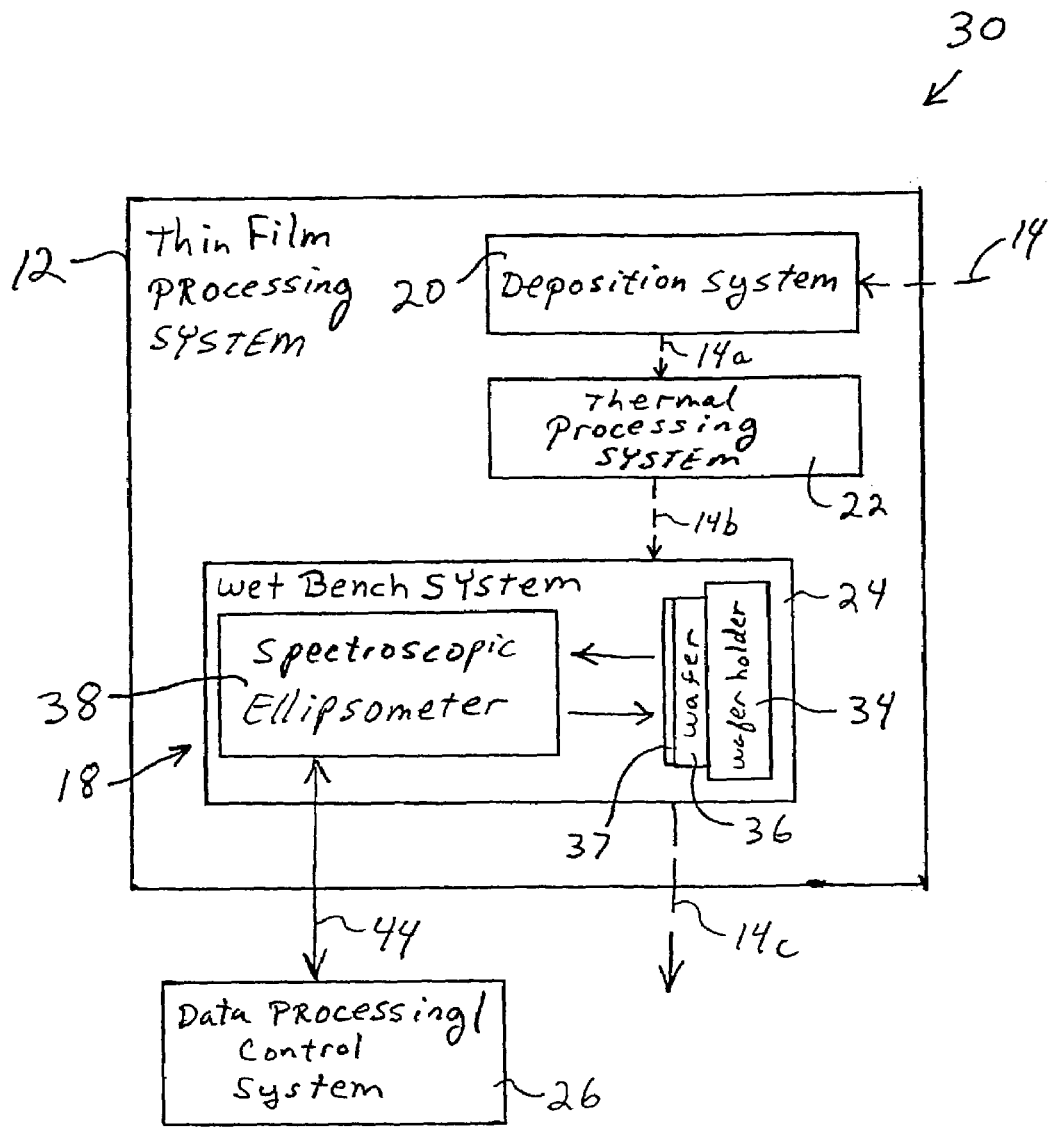
FIG. 2 is a block diagram of another exemplary thin film processing system for a wafer in accordance with the principles of the subject invention.

Referring now to FIG. 2, there is shown another embodiment of the subject invention. Particularly, there is depicted a thin film processing system for a wafer or substrate generally designated 30. The thin film processing system 30 utilizes the same principles and/or functions at least in the same manner as the system 10 of FIG. 1 described above. Therefore, the description of the system 10 is applicable to the system 30. The system 30 includes the processing area 12 that is operative, configured and/or adapted to allow thin film processing in the same manner as the processing chamber 12 of the system 10.

In the thin film processing system 30 of FIG. 2, the metrology system 18 is disposed in the wet bench system 24. Moreover, the metrology system 18 is particularly a spectroscopic ellipsometer 38. It should be appreciated that while other metrology tools may be used that are operative to provide and/or obtain the same measurement data as a spectroscopic ellipsometer 38, the subject invention preferably uses a spectroscopic ellipsometer 38 and such will be described herein.

A wafer holder 34 is shown disposed in the wet bench system 24 and is operative, configured and/or adapted to releasably retain a wafer 36. The wafer 36 is shown having a thin film 37 thereon, having been processed by the deposition system 20 and the thermal processing system 22. While the thin film 37 is shown as a single layer thin film, the thin film 37 is representative of a multi-layer thin film.

In the system 30, the in-situ or in-line metrology system 18 within or as part of the wet bench system 24 is an ellipsometer and, more particularly, a spectroscopic ellipsometer 38. The spectroscopic ellipsometer 38 is operative, configured and/or adapted to perform spectroscopic ellipsometry metrology on the sample (i.e. a wafer/substrate 36) while in the processing system 30, particularly the processing area 12 and, more particularly the wet bench system 24. Of course, the spectroscopic ellipsometer 38 may be provided in the other systems as indicated above with respect to a metrology system in the thin film processing system 10 of FIG. 1. Measurement of the wafer 36/thin film 37 by the spectroscopic ellipsometer 38 is represented by two arrows: one of which emanates from the spectroscopic ellipsometer 38; the other of which emanates from the wafer 36/thin film 37.

The spectroscopic ellipsometer 38 utilizes spectroscopic ellipsometry, which is a very sensitive surface and thin film measurement technique that uses polarized light. It derives is sensitivity from a determination of the relative phase change in a beam of reflected polarized light. Spectroscopic ellipsometry, as performed by the spectroscopic ellipsometer 38, provides data regarding the sample under test or measurement. It provides the ability to acquire data in special regions where the measure data are most sensitive to the model parameters that are to be determined.

The thin film processing system 30 and/or its various components including the spectroscopic ellipsometer 38 are under the control of the data processing/control system 26. Because the subject invention is described in connection with the in-situ spectroscopic ellipsometer 38, a bi-directional communication line 44 is shown between the data processing/control system 26 and the spectroscopic ellipsometer 38. The data processing/control system 26 is thus operative, configured and/or adapted to provide control signals to the spectroscopic ellipsometer 38 in order to obtain the spectroscopic ellipsometer metrology data. The obtained spectroscopic ellipsometer metrology data is provided to the data processing/control system 26 which calculates the various data as indicated herein (e.g. penetration depth) and provides the results as required. The data processing/control system 26 may utilize the data for modifying the thin film process, among other uses.

Figure 3:
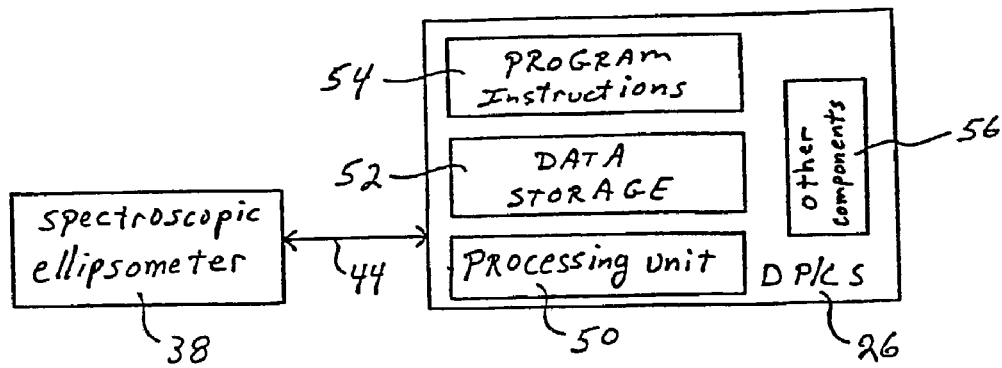
FIG. 3 is a block diagram of a portion of the subject invention.

As shown in FIG. 3, the data processing/control system 26 includes a processing unit 50 such as a microprocessor, processing means, processing unit and/or the like such as is known in the art. The processing unit 50 is operative, configured and/or adapted to provide the necessary processing and/or control of the system 26 and communications, including data transfer, between the spectroscopic ellipsometer 38 and the system 26. The processing unit 50 is under the control of appropriate program instructions 54 (i.e. software). The processing unit 50 executes the program instructions for the functionality, including the various calculations, described herein. The data processing/control system 26 also has data storage 52 that is operative to store data such as obtained data, calculated data and/or the like. The data processing/control system 26 also include other components 56 that provide the necessary functionality as described herein such as communication of results to other devices for human interpretation.

The spectroscopic ellipsometer 38 measures the change in polarization state of light reflected from the surface of the wafer 36. The measured values are expressed as psi ($\Psi$) and delta ($\Delta$). These values are related to the ratio of Fresnel reflection coefficients $R_p$ and $R_s$ for p- and s-polarized light, respectively in accordance with the following equation:

$$\rho = R_p/R_s = \tan(\Psi)e^{i\Delta}.$$

Because ellipsometry measures the ratio of the two values, it can be highly accurate and very reproducible. Because the ratio is a complex number, it also contains phase information ($\Delta$), which make the measurement very sensitive. There are several factors that determine the limits on the information about a given sample that can be obtained by ellipsometry. Ellipsometry works best for film characterization when thickness is not too much smaller or larger than the wavelength of the light used for the measurement. For instance, films from about 50 Angstroms to about several thousand-Angstroms thick are much simpler to characterize in general.

Also, roughness features on the sample's surface or a film interfaces should be less than ~10% of the probe beam wavelength for the ellipsometric analysis to be valid. Larger features can cause depolarization of the reflected beam. Finally, the thickness of films under investigation should vary by no more than ~10% over the width of the spot on the sample surface, or the assumption of parallel interfaces of the film will not be valid, and the calculated data cannot be expected to match the experimental data.

As indicated above, ellipsometry uses polarized light for measurements, i.e. an electromagnetic plane wave, which is a solution of Maxwell's equations for electromagnetic fields. Maxwell's equations for non-conducting, non-dispersive medium appear as follows:

$$\nabla \cdot E = 0$$

$$\nabla \cdot B = 0$$

$$\nabla \times E + (1/c)(\partial B/\partial t) = 0$$

$$\nabla \times B - (\mu \in /c)(\partial E/\partial t) = 0$$

where E and B are the electric and magnetic fields, c is the speed of light, $\mu$ and $\in$ are the permeability and dielectric function, respectively. It is assumed that the medium of propagation is isotropic.

These equations can be combined to produce the wave equation for the electric field:

$$\nabla^2 E - (1/v_2)(\partial^2 E/\partial t^2) = 0$$

where v is the optical impedance:

$$v = (c/(\mu \in))^{1/2}$$

A solution of the electric wave equation is the electromagnetic plane wave:

$$E(r,t) = E_0 \exp\{q(i2\pi n'/\lambda) \cdot r\} \exp(-i\omega t)$$

where q is a unit vector along the direction of wave propagation, n' is the complex index of refraction n+ik, $\lambda$ is the wavelength of the light in vacuum, $\omega$ is the angular frequency of the wave, and $E_0$ is a complex vector constant responsible for the amplitude and polarization state of the wave. The E-field and the B-field, and the direction of propagation are all orthogonal with respect to each other. Polarization states are usually defined in terms of the direction and phase of the E-field vector only. Regarding the complex index of refraction (i.e. n' where n'=n+ik) is non-zero, the amplitude of the wave (incident probing light) will decay exponentially as it propagates through the thin film or thin films, according to the to the following expression:

$$E \propto e^{(-2\pi k z/\lambda)}$$

where z is the distance of propagation into the thin film (or thin films), k is the extinction coefficient or constant (the damping coefficient or constant, or the absorption coefficient or constant), and λ is the wavelength (in the same units as the distance of propagation). The wave will decay 1/e of its original amplitude after propagating a distance $D_p$, the penetration depth where:

$$D_p = (\lambda/2\pi k).$$

This is an important concept with regard to the principles of the subject invention, as many material exhibit large values of the extinction coefficient such that the light beam may penetrate a few hundred Angstroms or less into the material (i.e. thin film).

According to the principles of the subject invention, the spectroscopic ellipsometry provides a technique for measuring optical constants. The subject technique requires an accurate model of the measurement process to analyze the measure data. The key components of all ellipsometric models are the optical constants of the substrate and sample layers, and the thickness of the layers. Such optical constants may be in the near-UV, visible and near-IR wavelength ranges.

The extinction coefficient k is a unique function of the composition and quality of the thin film or films. Therefore, for a given composition, there will be a unique k that is defined, as well as a refractive index n. The spectroscopic ellipsometer 38 is operative, configured and/or adapted to obtain the extinction coefficient k and the refractive index n. From these measurements, the data processing/control system 26 calculates the penetration depth. As indicated above, the penetration depth is a unique function of the extinction coefficient k. For uniform (or constant composition, constant k) film, the penetration depth is defined for a particular depth is defined for a given incident wavelength. If composition of the film varies (or k varies—i.e. not a constant value) then the penetration depth will vary as a result. Penetration depth is thus used for monitoring film thickness and quality, regardless of the number of film layers.

The subject invention is thus operative, configured and/or adapted to provide composition and/or thickness measurements of thin films such as silicides formed by silicidation on various sample structures. In one form, verification of the metalization scheme (e.g. thin film deposition) on the wafer is obtained. Particularly, penetration depth is thus effectively used for monitoring thin film composition and quality. Without being exhaustive, and referring to FIGS. 4A, 4B, 4C and 4D, various types of thin films can be non-destructively analyzed in-situ or in-line with the subject invention (i.e. by determining penetration depth). As well, FIGS. 4A through 4D are examples of the type of thin film processing achievable by the thin film processing systems 10 and 30.

Figure 4A:
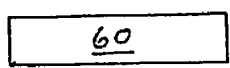
FIGS. 4A-4D depicts an exemplary wafer after thin film processing and/or an illustration of the types of wafers with or without a thin film structure that the subject invention can measure.

In FIG. 4A, a wafer 36A is shown consisting of a bare silicon substrate or wafer 60. This may be considered a reference material. This is the form as it enters the thin film processing system 10/30. As such, measurement by the metrology system 18/spectroscopic ellipsometer 38 may be taken therefrom if necessary. In summation, a measurement of the bare silicon substrate 60 may be taken by the spectroscopic ellipsometer 38 as a baseline if desired.

Figure 4B:
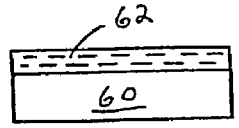
Figure 4C:
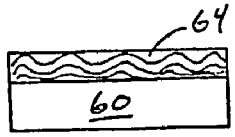
Figure 4D:
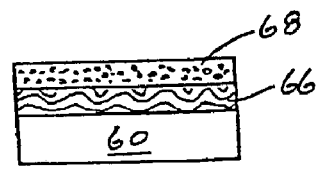

In FIG. 4B, a wafer 36B is shown having the silicon substrate 60 with a nickel thin film 62 thereon. The thin film 62 was formed thereon in the deposition system 20. The subject invention monitors penetration depth as calculated through measurements obtained by the spectroscopic ellipsometer 38. This may occur in the deposition system 20 (i.e. in-situ). In FIG. 4C, a wafer 36C is shown having the silicon substrate 60 with a nickel silicide thin film 64 thereon. The thin film 64 was formed thereon in the thin film processing system. In FIG. 4D, a wafer 36D is shown having the silicon substrate 60 with a nickel silicide thin film 66 and another type of thin film 68 thereon. The thin films 66 and 68 were formed thereon by the thin film processing system. The subject invention monitors penetration depth as calculated through measurements obtained by the spectroscopic ellipsometer 38 while the wafer 36D is in the thin film processing system.

Figure 5:
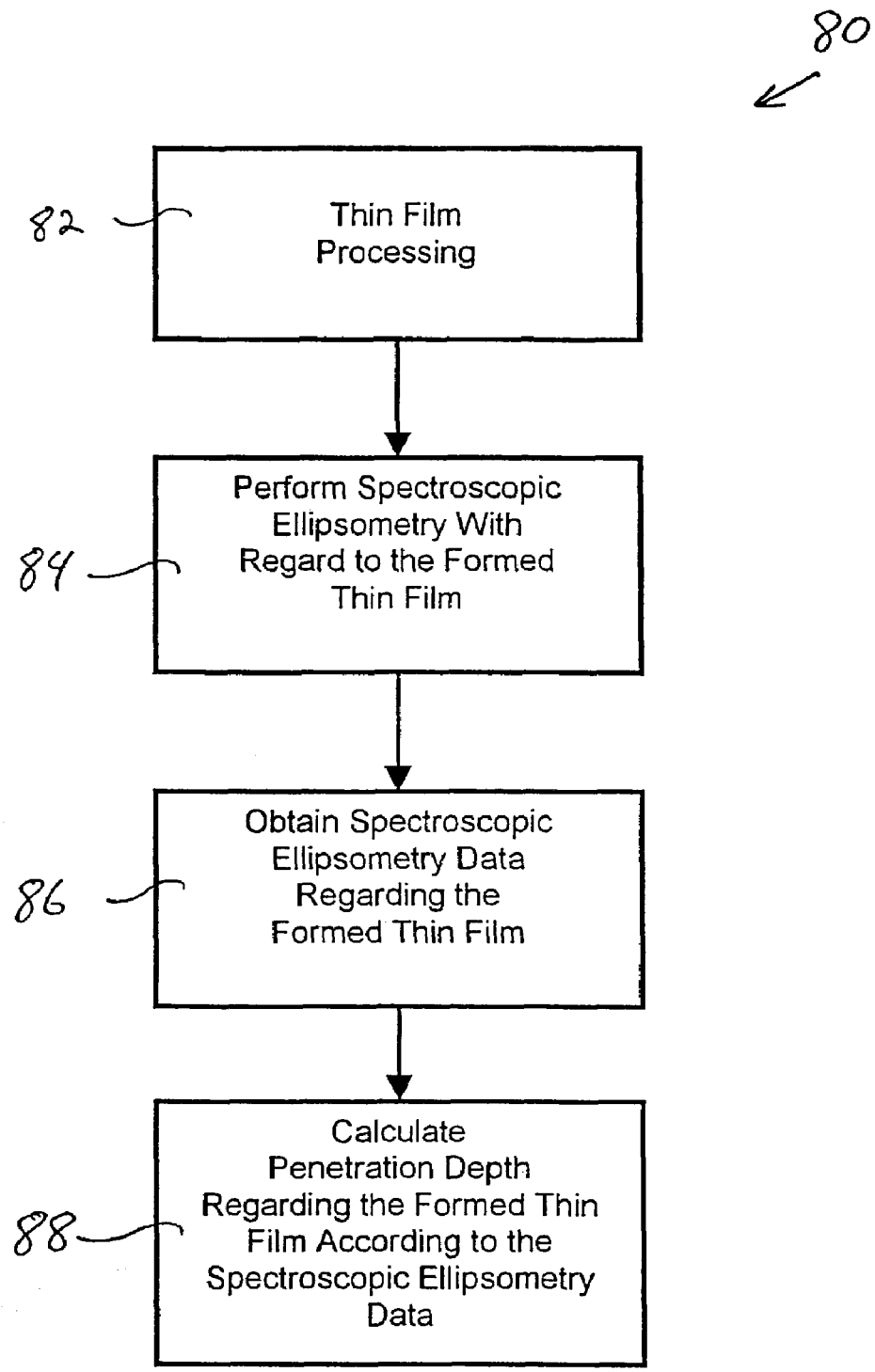
FIG. 5 is a flowchart of an exemplary manner of operation of the subject invention.

Referring now to FIG. 5, there is depicted a flowchart, generally designated 80, of an exemplary manner of operation of the subject invention. It should be appreciated that the steps shown and/or described herein are not necessarily requisite for the subject invention to operate. Also, the exemplary manner of operation will be described in connection with the system 30, however the system 10 and other systems made in accordance with the principles of the subject invention can carry out the various steps. It should also be appreciated that the manner of operation is with regard to a processing chamber having a substrate or wafer holder operative to releasably retain a substrate or wafer and a processing device operative to provide a thin film, silicidation, metalization or the like processing on and/or with regard to the substrate or wafer. Further, in accordance with the principles of the subject invention, a metrology device and, preferably a spectroscopic ellipsometer, is provided and/or disposed in the processing chamber. Furthermore, the manner of operation depicted in the flowchart 80 of FIG. 5 is a simplified version of the process.

In step 82, a substrate or wafer (hereinafter, "wafer") has been processed such that a thin film, such as a silicide (in which case a silicidation process has been or is being performed), metalization or the like (collectively and hereinafter "thin film") or multiple thin film layers is formed on the wafer. In step 84, spectroscopic ellipsometry (metrology) is performed by a spectroscopic ellipsometer with regard to the thin film. The spectroscopic ellipsometer obtains, in step 86, spectroscopic ellipsometry data with respect to the thin film. Particularly, but not necessarily exclusively, the spectroscopic ellipsometer obtains an extinction coefficient (k) with respect to the thin film. Thereafter, penetration depth ($D_p$) is calculated according to $D_p = (\lambda/2k\pi)$. This provides data regarding at least one of the composition, quality and thickness of the thin film. The process may be repeated as necessary for monitoring the same thin film or subsequent thin films formed on the same substrate (i.e. over the last formed thin film).

While this invention has been described as having a preferred design and/or configuration, the subject invention can be further modified within the spirit and scope of this disclosure. This application is therefore intended to cover any variations, uses, or adaptations of the invention using its general principles. Further, this application is intended to cover such departures from the subject disclosure as come within known or customary practice in the art to which this invention pertains and which fall within the limits of the appended claims.

What is claimed is:

1. A thin film processing system for a wafer comprising:
   a processing area including a deposition system, a thermal processing system and a wet bench area operative to perform a thin film formation process including thin film deposition on a wafer; and
   a spectroscopic ellipsometer disposed in said processing area and operative to perform in situ metrological measurement of at least one aspect of the thin film formation process wherein at least one of composition, quality and thickness of a formed thin film is obtained.

2. The thin film processing system of claim 1, wherein said spectroscopic ellipsometer is operative to perform metrological measurement including obtaining an extinction coefficient (k).

3. The thin film processing system of claim 2, wherein said spectroscopic ellipsometer is operative to calculate depth penetration (Dp) according to $Dp=(\lambda/2k\pi)$.

4. The thin film processing system of claim 1, wherein said thin film processing area is operative to perform silicidation formation on the wafer.

5. The thin film processing system of claim 1, wherein said spectroscopic ellipsometer is disposed in a thin film deposition system of the thin film processing system.

6. The thin film processing system of claim 1, wherein said spectroscopic ellipsometer is disposed in a thermal processing system of the thin film processing system.

7. The thin film processing system of claim 1, wherein said spectroscopic ellipsometer is operative to perform the in situ metrological measurement during the thin film deposition.

8. The thin film processing system of claim 1, where said spectroscopic ellipsometer is operative to perform the in situ metrological measurement during thermal processing of the thin film.

* * * * *